(12) United States Patent
Harris et al.

(10) Patent No.: US 7,920,912 B2
(45) Date of Patent: Apr. 5, 2011

(54) SYSTEM AND METHOD FOR TRIGGERING A DEVICE BASED ON AN ELECTROCARDIOGRAM SIGNAL

(75) Inventors: Mark Steven Harris, Rocky Hill, CT (US); Richard Alan Mentelos, Guilford, CT (US)

(73) Assignee: Ivy Biomedical Systems, Inc., Branford, CT (US)

( * ) Notice: Subject to any disclaimer, the term of this patent is extended or adjusted under 35 U.S.C. 154(b) by 1174 days.

(21) Appl. No.: 11/300,959

(22) Filed: Dec. 15, 2005

(65) Prior Publication Data

US 2007/0142734 A1  Jun. 21, 2007

(51) Int. Cl.
*A61B 5/05* (2006.01)
(52) U.S. Cl. ........ 600/428; 600/516; 600/510; 600/517; 600/514; 600/509; 600/508
(58) Field of Classification Search .......... 600/428, 600/509, 516, 517, 510
See application file for complete search history.

(56) References Cited

U.S. PATENT DOCUMENTS

| | | | |
|---|---|---|---|
| 3,759,248 A * | 9/1973 | Valiquette | 600/516 |
| 3,885,552 A * | 5/1975 | Kennedy | 607/27 |
| 3,903,874 A * | 9/1975 | Shakespeare | 600/508 |
| 3,939,824 A | 2/1976 | Arneson et al. | |
| 4,245,647 A * | 1/1981 | Randall | 600/436 |
| 6,070,097 A * | 5/2000 | Kreger et al. | 600/521 |
| 6,163,724 A * | 12/2000 | Hemming et al. | 607/28 |
| 6,347,245 B1 | 2/2002 | Lee et al. | |
| 6,463,326 B1 | 10/2002 | Hartley et al. | |
| 6,640,246 B1 | 10/2003 | Gary, Jr. et al. | |
| 2003/0001099 A1 | 1/2003 | Coles et al. | |
| 2003/0045907 A1* | 3/2003 | MacDonald | 607/9 |
| 2004/0172080 A1 | 9/2004 | Stadler et al. | |

FOREIGN PATENT DOCUMENTS

WO   WO2004/084722   10/2004

OTHER PUBLICATIONS

International Search Report and Written Opinion, mailed from the International Search Authority on Apr. 18, 2007.

* cited by examiner

*Primary Examiner* — Tse Chen
*Assistant Examiner* — Joel F Brutus
(74) *Attorney, Agent, or Firm* — K&L Gates LLP

(57) ABSTRACT

A system and method for triggering an external device in response to an electrocardiogram signal. In one embodiment the method includes determining a peak in the electrocardiogram signal, determining if the electrocardiogram signal is rising or falling at the peak in the signal and triggering a device in response to the rising or falling peak. In one embodiment of the invention an external trigger signal is produced only a rising peak is detected. In one embodiment, the system includes a microprocessor, a peak detector and a trigger circuit. The trigger circuit outputs a trigger signal to an external device when signaled by the peak detector and not inhibited by a signal from the microprocessor.

14 Claims, 3 Drawing Sheets

SYSTEM AND METHOD FOR TRIGGERING A DEVICE BASED ON AN ELECTROCARDIOGRAM SIGNAL

TECHNICAL FIELD OF THE INVENTION

This invention relates to the field of trigger monitors and more specifically to the triggering of an external device in response an electrocardiogram signal.

BACKGROUND OF THE INVENTION

Certain medical conditions require that the heart be imaged for diagnostic purposes. Frequently, the patient's heart is imaged with a gamma camera. A gamma camera uses gamma rays to produce an image of the heart at a specific point in the heart cycle. For example, the physician might want to trigger the camera to image the heart on a P-wave, a T-wave or a QRS complex. In certain diseases, the T-wave can be large and present detectors may mistake a T-wave for a QRS complex. Thus, if the physician is looking for a QRS complex, the camera may be triggered twice: once on a QRS complex and once on the abnormal T-wave.

The radiation from the cameras is harmful in large doses. Therefore, the treating physician wants to ensure that the camera is only imaging at the desired point in the cardiac cycle, the QRS complex for example, to reduce the number of images taken.

The present invention addresses the problems associated with triggering a device based on a waveform in the cardiac cycle.

SUMMARY OF THE INVENTION

In one aspect, the invention relates to a system for selectively triggering a device in response to an electrocardiogram signal. The system, in one embodiment, includes a microprocessor, a peak detector and a trigger circuit. The trigger circuit outputs a trigger signal to an external device when signaled by the peak detector and not inhibited by a signal from the microprocessor.

In one embodiment of the invention the microprocessor inhibits the trigger circuit only when the microprocessor determines that at the peak the electrocardiogram signal is decreasing in value. In another embodiment, the system further includes a pre-peak filter. In still another embodiment, the pre-peak filter includes a differentiator and a full wave rectifier. In yet another embodiment of the invention, the system triggers an external imaging device.

Another aspect of the invention relates to a method for triggering an external device in response to an electrocardiogram signal. In one embodiment the method includes determining a peak in the electrocardiogram signal, determining if the electrocardiogram signal is rising or falling at the peak of the signal and triggering a device in response to the a rising peak.

BRIEF DESCRIPTION OF THE FIGURES

The foregoing and other objects, aspects, features, and advantages of the invention will become more apparent and may be better understood by referring to the following description taken in conjunction with the accompanying drawings, in which.

DETAILED DESCRIPTION OF THE INVENTION

Figure 1:
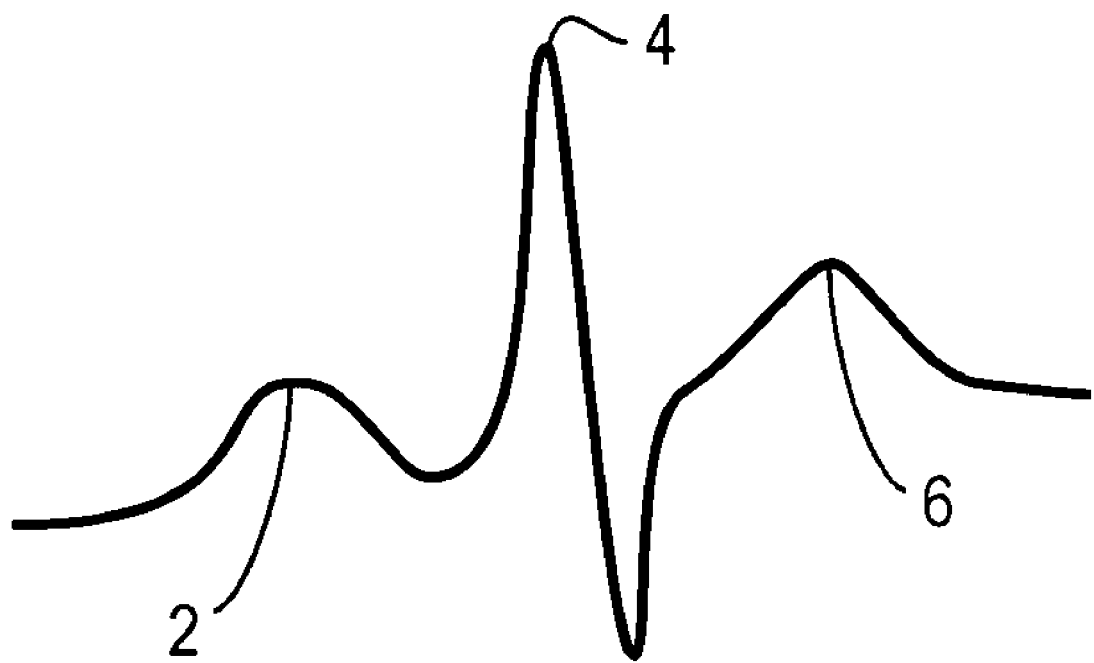
FIG. 1 is a depiction of an electrocardiogram signal.

Referring to FIG. 1, FIG. 1 is a depiction of the voltage time relationship of an electrocardiogram signal. The figure depicts the spread of electrical activity through the heart during a heartbeat. The P-wave 2 corresponds to the spread of electrical activity over the atria and marks the beginning of the heart's contraction. The QRS complex 4 corresponds to the spread of the electrical activity over the ventricles and marks the beginning of the contraction. The T-wave 6 corresponds to the recovery phase of the ventricles. The QRS complex 4 has a markedly different shape from the P-wave and T-wave. For example, while the P-waves and T-waves have steep trailing slopes, the QRS complex 4 has a relatively steep slope on both edges.

Figure 2:
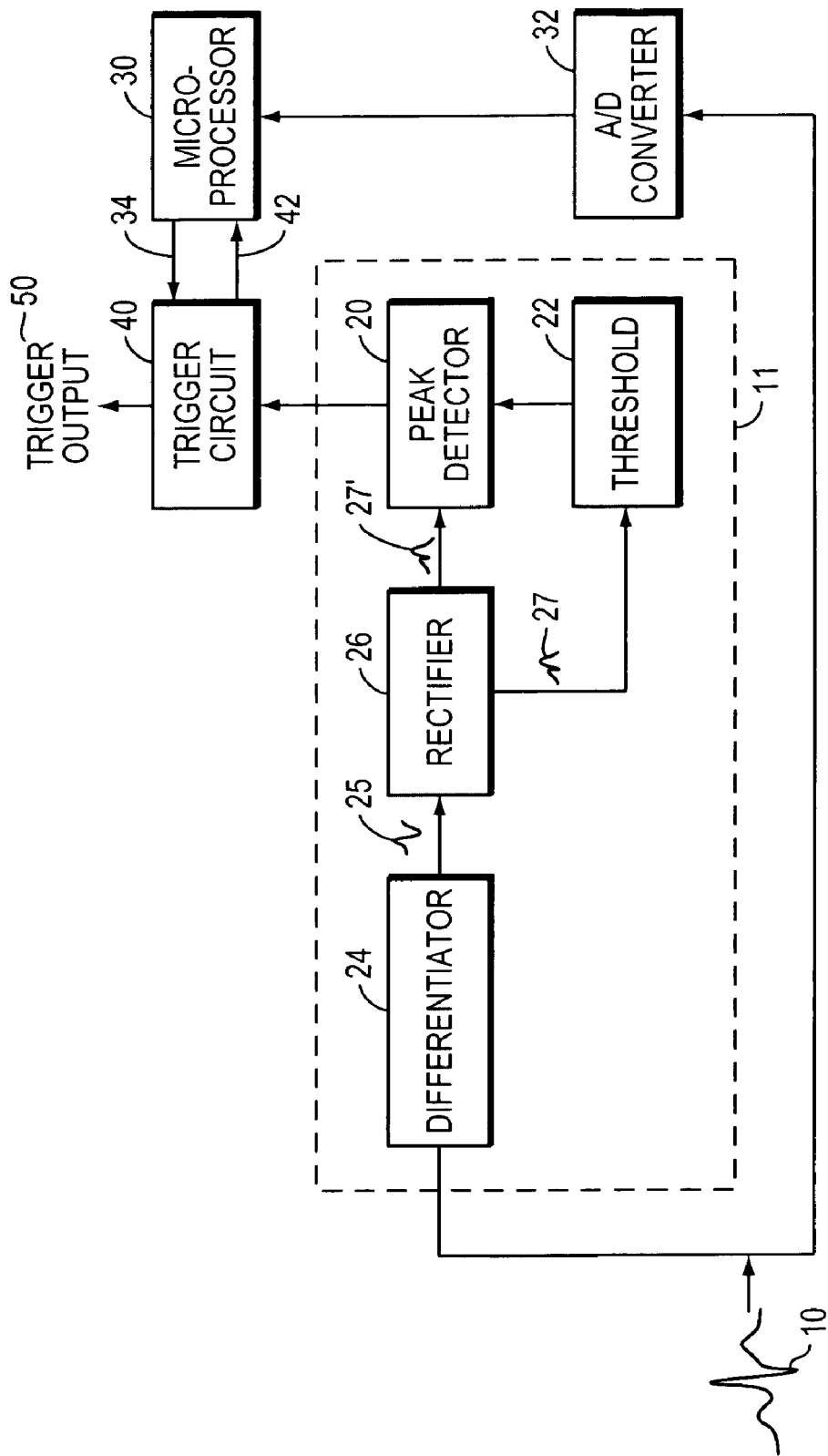
FIG. 2 is a block diagram of an embodiment of the system for selectively triggering a device in response to an electrocardiogram signal of the invention.

An embodiment of the invention is depicted in FIG. 2. In this embodiment an electrocardiogram signal 10 is passed to both the peak detection circuitry 11 and a microprocessor 30 in order to determine whether a trigger circuit 40 is to send a trigger signal 50 to an external device (not shown). In this embodiment the peak detection circuitry 11 includes a differentiator 24 in electrical communication with a rectifier 26. The rectifier 26 is in turn in communication with a threshold circuit 22 and a peak detector 20. The peak detector 20 is in turn in communication with the trigger circuit 40.

The electrocardiogram signal 10 which is passed to the microprocessor 30 is first an input signal to an analog to digital (A/D) converter 32. The A/D converter 32 is in turn in communication with a digital input of the microprocessor 30. The microprocessor 30 is also in two way communication with the trigger circuit 40.

In this embodiment, in operation, the electrocardiogram signal 10 obtained from electrodes on a patient is passed to both the differentiator 24 and the A/D converter 32. The differentiator 24 differentiates the electrocardiogram signal 10 and produces an output signal 25 which has upwardly pointing and a downwardly pointing peaks corresponding to the inflection points of the rising and falling segments, respectively, of each of the peaks in the electrocardiogram This differentiated electrocardiogram signal is rectified by a rectifier 26. Rectification is equivalent to taking the absolute value of the differentiated signal. Thus the rectifier 26 produces an output signal 27 having two positive peaks, instead of an upwardly pointing and downwardly pointing peak. The rectifier 26 sends this output signal 27, 27' to both a threshold circuit 22 and a peak detector 20.

The threshold circuit 22 then analyzes the two peaks of the output signal of the rectifier 26. The threshold circuit 22 only selects peaks between seven and seventy milliseconds in length. If the first peak is greater than sixty percent of the second peak, the threshold circuit 22 signals the peak detector 20 to locate the peak of the signal in order to cause the trigger circuit 40 to transmit a trigger signal 50 to the external device. This peak comparison is designed to prevent false triggers on T-waves and P-waves, because the P-waves and T-waves have steeper trailing slopes than leading slopes. Thus the system will not trigger initially on the peak corresponding to the leading slope of a P-wave or a T-wave.

Concurrently with the peak detection, the electrocardiogram signal 10 is digitized by the A/D converter 32. In the embodiment shown the A/D converter 32 is an 800 Hz constant trigger A/D converter. This digitized electrocardiogram signal is sent to the microprocessor 30 for analysis. The microprocessor 30 then captures and analyzes the digital signal from the A/D converter 32 only when the trigger circuit 40 notifies the microprocessor 30 by way of a timing signal 42 that a valid peak (having the correct predetermined amplitude) has been detected by the peak detector 20.

The problem arises that under certain conditions the T-wave can have certain properties that make it appear to be similar to the R-peak in the QRS complex. To avoid mistriggering on this form of T-wave, the microprocessor 30 determines the amplitude change in the undifferentiated electrocardiogram 10. If the electrocardiogram signal 10 is increasing in value at the time the peak is found, the microprocessor 30 validates that the peak is part of a QRS complex. In this case, in one embodiment, the microprocessor 30 does nothing since the peak that has been found is the correct peak for a QRS wave and a trigger of the external device should be allowed to occur.

In this embodiment the trigger circuit 40 remains enabled, and the trigger circuit 40 produces the trigger output 50. However, if the electrocardiogram signal 10 is decreasing in value, the microprocessor 30 decides that the system is examining a T-wave or P-wave and the microprocessor 30 sends an inhibit signal 34 to the trigger circuit 40 to prevent the trigger output signal 50 from being transmitted.

Once the microprocessor 30 validates two successive sets of peaks as QRS complexes, the microprocessor 30 will send the inhibit signal 34 to the trigger circuit 40 during P-waves and T-waves. Two successive sets of double peaks corresponding to QRS complexes are needed to ensure that a single noise spike does not falsely cause the system to inhibit the trigger output 50 on QRS complexes. In this way the trigger signal will only be produced when a QRS complex is detected and the trigger circuit 40 is deactivated when the microprocessor 30 determines that what has been detected is a P-wave or T-wave.

The triggering system also works if the polarity of the waves is reversed. For example, if the leads are reversed on a healthy patient, the signal polarity will be inverted. When the QRS complex of the electrocardiogram signal 10 is pointing downward, the trigger circuit 40 will remain enabled when the electrocardiogram signal 10 is decreasing in value.

Figure 3:
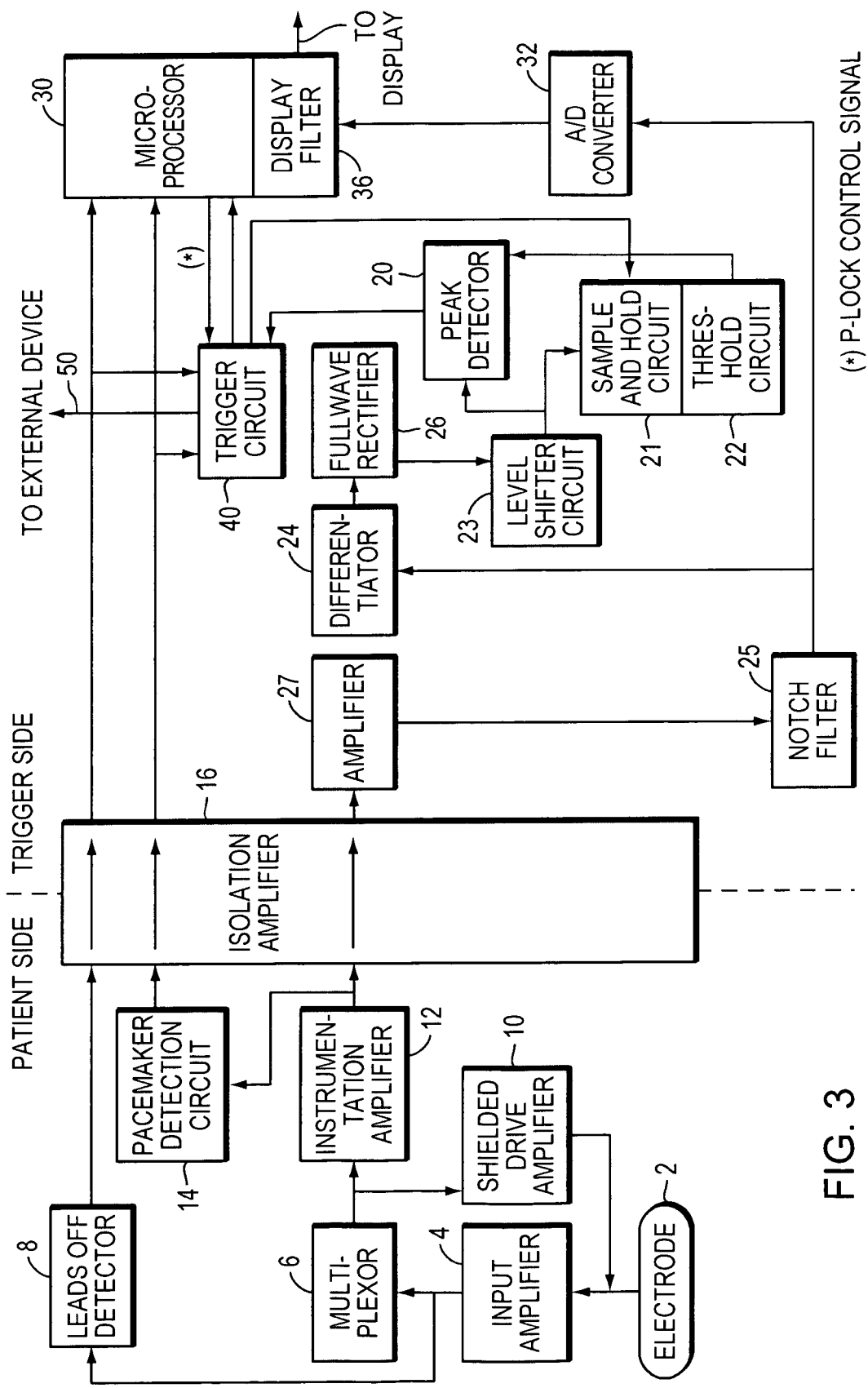
FIG. 3 is a block diagram of another embodiment of the system for selectively triggering a device in response to an electrocardiogram signal of the invention.

FIG. 3 depicts an embodiment of an entire electrocardiogram triggering circuit using the method of the invention. The system may be considered to be broken into two portions, a patient side and a trigger side. These two sides are connected to each other through isolation amplifiers 16 to prevent electrocution of the patient in the event of an electrical fault.

Considering the patient side first, the patient has three electrodes 2 attached to his or her body. Different pairs of these electrodes 2 are used to detect the electrical activity in the heart. Each electrode 2 detects and sends an electrocardiogram signal 10 to a respective input amplifier 4 which pre-amplifies the signal before sending the pre-amplified signal to a multiplexor 6.

The multiplexor 6 is used by the clinician to select the pairs of electrodes which will be used to measure the electrocardiogram. In the embodiment shown the multiplexor 6 is an analog multiplexor. However a digital multiplexor or simple switch may also be used. The output signal from the multiplexor 6 is the input signal to a shielded drive amplifier 10 and an instrumentation amplifier 12. The shielded drive amplifier 10 minimizes the effects of patient cable capacitance. The shielded drive amplifier 10 examines common mode signals and drives the shield of the patient cable in phase with the common mode signal. The end result is a reduction in common mode noise and cable movement artifact.

The instrumentation amplifier 12 amplifies the electrocardiogram signal 10 to the desired amplitude. The output signal from the instrumentation amplifier 12 is the input signal for the trigger side circuitry through the isolation amplifiers 16, and the input signal for a pacemaker detection circuit 14. The pacemaker detection circuit 14 used in this embodiment of the invention is a standard pacemaker circuit used in most electrocardiogram monitors. The pacemaker detection circuit 14 looks at the width of the peak signal to determine if a patient has a cardiac pacemaker. If the patient has a cardiac pacemaker, the cardiac pacemaker will generate a very sharp stimulatory signal which the pacemaker detection circuit 14 will detect. In response, the pacemaker detection circuit 14 generates an output signal each time the cardiac pacemaker triggers. This signal which is also an input signal to the microprocessor 30 and the trigger circuit 40 through the isolation amplifiers 16 provides information used by the trigger circuit 40 to prevent a trigger signal from being generated by the trigger circuit 40 in response to a cardiac pacemaker discharge. The output signal of the pacemaker detection circuit 14 is also sent to the microprocessor 40 and the pacemaker output signal displayed on the monitor of the display filter 36. In one embodiment, the display shows a flashing heart when a beat is detected and a flashing heart with a "P" on it when a beat is preceded by a pacemaker.

The electrocardiogram signal from the input amplifier 4 is also the input signal to a leads off detector 8. The leads off detector 8 detects when an electrode has come loose and is no longer generating a proper signal. The leads off detector 8 produces a signal in response to a leads off condition and transmits it to the microprocessor 30 and trigger circuit 40 through the isolation amplifiers 16. If a leads off signal is received by the trigger circuit 40, the trigger circuit 40 does not generate a trigger output signal 50. The leads off detector 8 detects a detached lead by passing low current through the electrode 2. The electrode is considered unconnected if the voltage across the electrode is greater than three volts. In one embodiment, if a detached electrode is detected, the microprocessor 30 displays a LEADS OFF message for the user on the display attached to the display filter 36.

Once the signal from the instrumentation amplifier 12 passes through the isolation amplifiers 16 it is again amplified by amplifier 27 and through a notch filter 25 to remove 50-60 Hz line noise. The output signal from the notch filter 25 is the input signal to the differentiator 24. Although the trigger side in this embodiment is substantially as described in the previous embodiment, there are a few minor additions. This embodiment includes a level shifter circuit 23 between the full wave rectifier 26 and the peak detector 20 and the threshold circuit 22. The level shifter shifts the signal level to remove any DC offset. In addition, the signal to the threshold circuit 22 passes through a sample and hold circuit 21 before the threshold is determined. This sample and hold circuit 21 receives a signal from the trigger circuit 40 in order to establish an average running threshold for the QRS complex.

Similarly, the signal to the microprocessor 30 from the A/D converter 32 is passed through a display filter 36 and produced for display on a monitor 36 in real time. The display filter 36 eliminates hardware by having the microprocessor perform a low-pass filter function. Additionally, the display filter 36 helps reduce noise on the electrocardiogram and baseline for the display.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for selectively triggering a device in response to an electrocardiogram signal comprising:
    a microprocessor comprising a microprocessor digital input and a microprocessor control output;
    a peak detector comprising a peak detector input and a peak detector output; and
    a trigger circuit having a peak detection control input, a microprocessor control input and trigger output, the peak detection control input in communication with the peak detector output and the microprocessor control input in communication with the microprocessor control output,
    wherein said trigger circuit generates an output signal on the trigger output in response to a peak detection control input signal from the peak detector output and a microprocessor control input signal from the microprocessor control output,
    wherein the microprocessor control input signal inhibits the trigger output signal if the electrocardiogram signal has one of either a predetermined number of decreasing values in a positive R-wave or a predetermined number of increasing values in a negative R-wave and permits the trigger output signal in response to detecting two successive peaks in a differentiated single heartbeat if the electrocardiogram signal has a duration of between seven and seventy milliseconds between a predetermined threshold and a detected peak of the differentiated electrocardiogram signal, and
    wherein such detection is in response to a validation of at least two QRS complexes.

2. The system of claim 1 wherein the trigger circuit generates the trigger output when the peak detector input is asserted and the microprocessor control input is not asserted.

3. The system of claim 1 wherein the microprocessor control signal is asserted if the electrocardiogram signal is inverted and has a predetermined number of increasing values and not asserted if the electrocardiogram signal is inverted and has a predetermined number of decreasing values.

4. The system of claim 1 further comprising an A/D converter comprising an A/D converter input and an A/D converter output, wherein the digital converter output is in communication with the microprocessor digital input.

5. The system of claim 1 further comprising a pre-peak filter comprising a filter input and a filter output wherein the filter output is in communication with the peak detector input.

6. A system as defined in claim 5 wherein the pre-peak filter comprises a differentiator in communication with a full wave rectifier, the differentiator comprising a differentiator input and the full wave rectifier comprising a full wave output, the differentiator input being the pre-peak filter input and the full wave rectifier output being the pre-peak filter output.

7. A system as defined in claim 1 wherein the peak detector further comprises a peak threshold input.

8. A system as defined in claim 7 further comprising a threshold filter having a threshold input and a threshold output, the threshold output in communication with the peak threshold input and the threshold input in communication with the pre-peak filter output.

9. A system as defined in claim 8 wherein the threshold filter generates a threshold output signal when the threshold input signal comprises two peaks, the first being no less than sixty percent of the second.

10. A system for imaging a patient in response to an electrocardiogram signal comprising
    a microprocessor comprising a microprocessor digital input and a microprocessor control output;
    a peak detector comprising a peak detector input and a peak detector output; and
    a trigger circuit having a peak detection control input, a microprocessor control input and trigger output, the peak detection control input in communication with the peak detector output and the microprocessor control input in communication with the microprocessor control output, and
    an imaging device, comprising an imaging input, wherein the imaging input is in communication with the trigger output
    wherein said trigger circuit generates an output signal on the trigger output in response to a peak detection control input signal from the peak detector output and a microprocessor control input signal from the microprocessor control output, and
    wherein the microprocessor control signal:
    inhibits the trigger output signal if the electrocardiogram signal has one of either a predetermined number of decreasing values in a positive R-wave or a predetermined number of increasing values in a negative R-wave and permits the trigger output signal in response to detecting two successive peaks in a differentiated single heartbeat if the electrocardiogram signal has a duration of between seven and seventy milliseconds between a predetermined threshold and a detected peak of the differentiated electrocardiogram signal, and
    wherein such detection is in response a validation of at least two QRS complexes.

11. The system of claim 10 wherein the microprocessor control signal is asserted if the electrocardiogram signal is inverted and has a predetermined number of increasing values and not asserted if the electrocardiogram signal is inverted and has a predetermined number of decreasing values.

12. The system of claim 10 wherein the imaging device is a gamma camera.

13. A method for selectively triggering a device in response to an electrocardiogram signal comprising the steps of:
    determining two successive peaks in a differentiated electrocardiogram signal in a single heartbeat;
    determining if the electrocardiogram signal is rising or falling at one peak;
    determining if the duration between a threshold and the one peak is between seven and seventy milliseconds within a single heartbeat inhibiting the trigger output signal if the electrocardiogram signal has one of either a predetermined number of decreasing values in a positive R-wave or a predetermined number of increasing values in a negative R-wave; and
    triggering a device in response to a validation of at least two QRS complexes and the determinations.

14. The method of claim 13 further comprising manipulating the electrocardiogram signal comprising;
    rectifying the electrocardiogram signal;
    filtering the rectified electrocardiogram signal; and
    selecting only filtered signals with two peaks,
    prior to determining the peak in the electrocardiogram.

* * * * *